US007195889B2

(12) United States Patent
Hembre et al.

(10) Patent No.: US 7,195,889 B2
(45) Date of Patent: Mar. 27, 2007

(54) PROCESS FOR STABILIZING ENZYMES WITH PHOSPHINE OR PHOSPHITE COMPOUNDS

(75) Inventors: Robert T. Hembre, Johnson City, TN (US); Paul S. Wagenknecht, San Jose, CA (US); Jonathan M. Penney, New York, NY (US)

(73) Assignee: Eastman Chemical Company, Kingsport, TN (US)

( * ) Notice: Subject to any disclaimer, the term of this patent is extended or adjusted under 35 U.S.C. 154(b) by 699 days.

(21) Appl. No.: 10/308,778

(22) Filed: Dec. 3, 2002

(65) Prior Publication Data
US 2003/0124696 A1 Jul. 3, 2003

Related U.S. Application Data

(62) Division of application No. 09/522,872, filed on Mar. 10, 2000, now Pat. No. 6,599,723.

(60) Provisional application No. 60/123,888, filed on Mar. 11, 1999.

(51) Int. Cl.
C12Q 1/26 (2006.01)
(52) U.S. Cl. ........................ 435/25; 435/69.2; 435/188; 435/189
(58) Field of Classification Search .................. 435/25, 435/69.2, 188, 189
See application file for complete search history.

(56) References Cited

U.S. PATENT DOCUMENTS

| 2,588,746 | A | * | 3/1952 | McKinley ...................... 175/4 |
| 3,860,484 | A | | 1/1975 | O'Malley |
| 4,221,869 | A | | 9/1980 | Vandecasteele et al. |
| 4,352,885 | A | | 10/1982 | Zeikus et al. |
| 4,526,661 | A | | 7/1985 | Steckhan et al. |
| 4,749,670 | A | | 6/1988 | Simon et al. |
| 5,777,008 | A | | 7/1998 | Pitteloud |
| 5,817,467 | A | | 10/1998 | Aoyama et al. |
| 6,599,723 | B1 | * | 7/2003 | Hembre et al. ............. 435/166 |
| 2004/0091985 | A1 | * | 5/2004 | Metcalf et al. ............. 435/189 |

OTHER PUBLICATIONS

Abril et al., "Hybrid Organometallic/Enzymatic Catalyst Systems: Regeneration of NADH Using Dihydrogen[1]," *J. Am. Chem Society*, 104:1552-54 (1982).
Aono, et al., "Photochemical Reduction of NADP to NADPH and Hyriogenation of 2-Butanone using 2,2'-Bipyridinium Salts as Electron Carriers," Inorganica Chimica Acta, 152:55-59 (1988).
Bhaduri et al., Coupling of Catalyses by Carbonyl Clusters and Dehydrogenases: Reduction of Pyruvate to L-Lactate by Dihydrogen, *J. Am. Chem Soc.*, 120:12127-12128 (1998).
Chenault, et al., "Regeneration of Nicotinamide Cofactors for use in Organic Synthesis," *Applied Biochemistry and Biotechnology*, 14:147-197 (1987).
Daigle et al., 1,3,5-Triaza-7-Phosphatricyclo[3.3.1.1$^{3,7}$]Decane and Derivatives, *Inorg. Synth.*, 32:40-45 (1998).
Darensbourg et al., "Water-Soluble Organometallic Compounds. 4. Catalytic Hydrogenation of Aldehydes in an Aqueous Two-Phase Solvent System Using a 1,3,5-Triaza-7-phosphaadamantane Complex of Ruthenium,", *Inorg. Chem.*, 33:200-208 (1994).
Dixon et al., "Enzymes," *Academic Press*, New York, 5:207-230 (1979).
Drauz et al., "B.5 Reduction Reactions," *Enzymes in Organic Synthesis*, p. 595-664 (1995).
Franke et al., "Tris(2,2'-bipyridyl-5-sulfonic acid)rhodium(III), an improved Redox Catalyst for the Light-Induced and the Electronchemically Initiated Enzymatic Reduction of Carbonyl Compounds," *Angew. Chem. Int'l Ed. Engl.*, 27:265-267 (1988).
Hernandez et al., "Water-soluble ruthenium complexes containing tris(m-sulfonatophenyl)phosphine (TPPTS). Preparation-of a series of [Ru(H)($\eta^6$-arene)(TPPTS)$_3$] and revisited procedures for previously described ruthenium-TPPTS compounds," *Journal of Molecular Catalysis A: Chemica*, 116:117-130 (1997).
Hummel et al., "Isolation of L-Phenylalanine dehydrogenase from *Rhodococcus* sp. M4 and its application for the production of L-phenylalanine," *Appl. Microbiol Biotechnol*, 26:409-416 (1987).
Jones et al., "Preparative-scale Reductions of Cyclic Ketone and Aldehyde Substrates of Horse Liver Alcohol Dehydrogenase with *in situ* Sodium Dithionite Recycling of Catalytic Amounts of NAD," *J.C.S. Chem. Comm.*, p. 856-857 (1972).
Kalck et al., "Use of Water-Soluble Ligands in Homogeneous Catalysis," *Advances in Organometallic Chemistry*, 34:219-285 (1992).
Keinan et al., "Thermostable Enzymes in Organic Synthesis. 2.[1] Asymmetric Reduction of Ketones with Alcohol Dehydrogenase from *Thermoanaerobium brockii*," J. Am. Chem. Soc., 108:162-169 (1986).
Mandler et al., "Solar Light Induced Formation of Chiral 2-Butanol in an Enzyme-Catalyzed Chemical System," *J. Am. Chem. Soc.*, 106:5352-5353 (1984).
Obon et al., "Retention and Regeneration of Native NAD(H) in Noncharged Ultrafiltration Membrane Reactors: Application to L-Lactate and Gluconate Production," *Biotech. Bioeng.*, 57:510-517 (1998).
Ohnishi et al., "Model of Formate-Dependent Biological Processes," *Tetrahedron Letters*, 22:1909-1912 (1977).
Oikonomakos et al., "Activator anion binding site in pyridoxal phosphorylae *b*: The binding of phosphite, phosphate, and flurorphosphate in the crystal.," *Protein Science*, 5:2416-2428 (1996).
Oppenheimer et al, "A Structure of Pyridine Nucleotides in Solution," *Proc. Nat. Aca.Sci. USA*, 68(12):3200-3205 (1971).

(Continued)

Primary Examiner—Ralph Gitomer
(74) Attorney, Agent, or Firm—Brett L. Nelson; Bernard J. Graves

(57) ABSTRACT

The invention relates to processes for stabilizing the activity of an enzyme, comprising mixing a phosphine or phosphite with an oxidoreductase enzyme.

14 Claims, No Drawings

OTHER PUBLICATIONS

Otuska, et al., "Regeneration of NADH and Ketone Hydrogenation by Hydrogen with the Combination of Hydrogenase and Alcohol Dehydrogenase," *Journal of Molecular Catalysis*, 51:35-39 (1989).

Ragg et al., "$^1$H-, $^{13}$C-, $^{31}$P-NMR studies and conformational analysis of NADP$^+$, NADPH coenzymes and of dimmers from electrochemical reduction of NADP$^+$,"*Ang. Chem. Int. Ed. Engl.*, 1076:49-60 (1991).

Simon et al., "Chiral Compounds Synthesized by Biocatalytic Reductions," *Angew. Chem. Int. Ed. Engl.*, 24:539-553 (1985).

Steckhan, "Electroenzymatic Synthesis," *Topics in Current Chemistry*, 170:83-111 (1994).

Steckhan et al., "Continuous Generation of NADH from NAD and Formate Using a Homogeneous Catalyst with Enhanced Molecular Weight in a Membrane Reactor**," *Angw. Chem. Int. Ed. Engl.*, 102:445-447 (1990).

Steckhan et al., "Analytical Study of a Series of Substituted (2,2'-Bipyridyl) (pentamethylcyclopentadienyl)rhodium and-Iridium Complexes with Regard to their Effectiveness as Redox Catalysts for the Indirect Electrochemical and Chemical Reduction of NAD(P)$^+$," *Organometallics*, 10:1568-1577 (1991).

Walsh, "Enzymatic Reaction Mechanisms," W.H. Freeman and Co., New York, p. 311-357 (1979).

Webb, "Enzyme Nomenclature 1992—Recommendations of the Nomenclature Committee of the International Union of Biochemistry and Molecular Biology on the Nomenclature and Classification of Enzymes," *Academic Press*, San Diego, p. 24-115 (1992).

Wilner et al., "Thermal and Photochemical Regeneration of Nicotinamide Cofactors and a Nicotinamide Model Compound Using a Water-soluble Rhodium Phosphine Catalyst," *J. Chem. Soc. Perkin Trans.*, 2:559-564 (1990).

Wong et al., "Enzyme-Catalyzed Organic Synthesis: NAD(P)H Cofactor Regeneration Using Ethanol/Alcohol Dehyrogenase/ Aldehyde dehyrogenase and Methanol/Alcohol Dehydrogenase/ Aldehyde Dehydrogenase/Formate Dehydrogenase[1]," *J. Org. Chem.*, 45:2816-2818 (1982).

Wong et al., "Enzymatic vs. Fermentative Synthesis: Thermostable Glucose Dehydrogenase Catalyzed Regeration of NAD(P)H for use in Enzymatic Synthesis[1]," *J. Org. Chem. Soc.*, 107:4028-4031 (1985).

Wong et al., Enzyme-Catalyzed Organic Synthesis: NAD(P)H Regeneration Using Dihydrogen and the Hydrogenase from *Methanobacterium thermoautotrophicum*, *J. Am. Chem. Soc.*, 103:6227-6228 (1981).

\* cited by examiner

PROCESS FOR STABILIZING ENZYMES WITH PHOSPHINE OR PHOSPHITE COMPOUNDS

CROSS REFERENCE TO RELATED APPLICATIONS

This application is a divisional application of and claims priority to U.S. patent application Ser. No. 09/522,872 filed Mar. 10, 2000 and now issued as U.S. Pat. No. 6,599,723, and also claims priority to U.S. Provisional Patent Application Ser. No. 60/123,888 filed Mar. 11, 1999, both of which are hereby incorporated herein by this reference.

FIELD OF THE INVENTION

This invention relates to methods for stabilizing enzymes.

BACKGROUND OF THE INVENTION

The present invention relates to catalytic processes for the use of $H_2$ as a reducing agent for organic compounds, in the presence of catalysts containing enzymes. Many man-made catalysts are known for reduction and/or hydrogenation reactions, but there are many limitations in the ability of the known catalysts to selectively reduce or hydrogenate one unsaturated functional group in the presence of another functional group. Moreover, most prior art catalysts and processes cannot selectively produce optically active products, as is highly desirable in the production of compositions for human or animal consumption, such as food or pharmaceuticals.

In contrast, many enzymes are capable of highly selective reduction of their natural substrates. In some cases enzymes catalyze unique transformations that require multiple steps by traditional synthetic methods. Moreover, a wide range of unnatural substrates, including a wide variety of unsaturated organic compounds, can be enzymatically reduced, with high chemo-, regio- and/or enantioselectivity, under mild reaction conditions. It is therefore highly desirable to employ enzymatic processes for reductions of unsaturated compounds of commercial interest, and especially for the preparation of chiral molecules, as taught by Simon et al. (*Ang. Chem. Int. Ed. Engl.* 1985, 24, 539–53). Unfortunately, most enzymes capable of catalyzing such reduction reactions require the presence of cofactors, which function as biological reducing agents. One broad class of enzymes capable of selective reduction and/or hydrogenation of unsaturated organic compounds are the nicotinamide dependent oxidoreductases, as discussed by Walsh (*Enzymatic Reaction Mechanisms* Freeman & Co., N.Y., 1979; pages 311–521).

Nicotinamide dependent oxidoreductases require the presence of nicotinamide cofactors. The structures of the naturally occurring nicotinamide cofactors, ($NAD^+$, $NADP^+$, NADH and NADPH) are shown below.

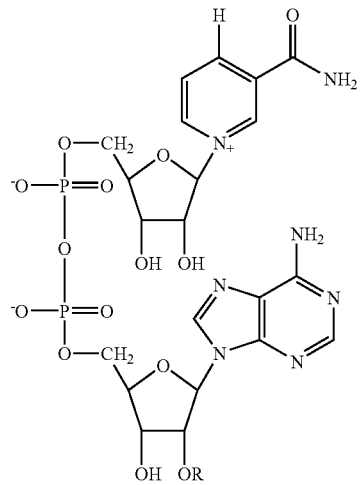

$NAD^+$: R = H
$NAD(P)^+$: R = $PO_3^{2-}$

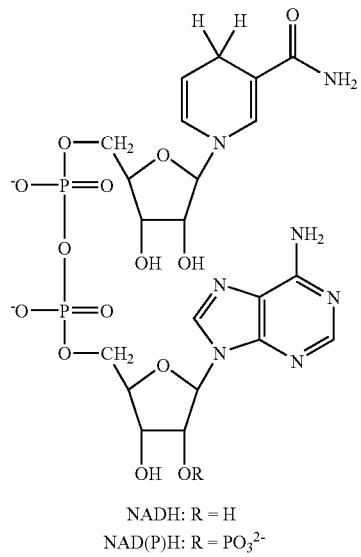

NADH: R = H
NAD(P)H: R = $PO_3^{2-}$

A reduced nicotinamide cofactor (NADH or NADPH) binds to the nicotinamide cofactor dependent enzyme, and transfers a "hydride" (two electrons and one hydrogen nucleus) to reduce a substrate that also binds to the enzyme. After the substrate is reduced, the enzyme releases the oxidized form of the nicotinamide cofactor ($NAD^+$ or $NADP^+$). Biological systems typically recycle the oxidized nicotinamide cofactors, by employing an external reducing agent, in combination with other enyzmes, to regenerate the reduced form of the nicotinamide cofactors. In these nicotinamide cofactors the nicotinamide ring (shown schematically immediately below) is the reactive group. To regenerate the reduced cofactor, an external reducing agent must transfer the equivalent of a "hydride" to the oxidized (pyridinium) form of the cofactor, regioselectively to form the reduced (1,4-dihydropyridine) form of the cofactor.

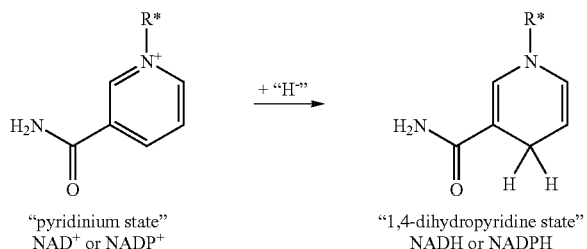

"pyridinium state"
NAD⁺ or NADP⁺

"1,4-dihydropyridine state"
NADH or NADPH

Although nicotinamide cofactor dependent enzymes and nicotinamide cofactors are present in all living organisms at low concentrations, they tend to be chemically unstable under non-biological conditions, and are extremely expensive in purified form. Because of their high cost, most industrial processes that seek to employ a combination of enzymes and nicotinamide cofactors must supply a method to regenerate the nicotinamide cofactors.

A number of methods for cofactor regeneration are known, as discussed by Chenault and Whitesides (*Appl. Biochem. Biotechnol.* 1987, 14, 147–97), and in *Enzymes in Organic Synthesis* K. Drauz, H. Waldeman, Eds.; VCH: Weinheim, 1995; pages. 596–665. The most widely used methods for cofactor regeneration employ a chemical reducing agent and second enzyme to regenerate the nicotinamide cofactors. For example, using glucose as a reducing agent, glucose oxidase has been shown to successfully regenerate NADP⁺/NADPH through up to $4 \times 10^4$ turnovers (see Wong, and Whitesides *J. Org. Chem.* 1982, 47, 2816–18; Wong et al., *J. Am. Chem. Soc.* 1985, 107, 4028–31; Obon et al., *Biotech. Bioeng.* 1998, 57, 510–17). Hummel et al., (*Appl. Microbiol. Biotechnol.* 1987, 26, 409–416) have shown that a combination of formate dehydrogenase and formate salts regenerates NADH from NAD⁺ with turnover numbers for the reduced cofactor as high as $6 \times 10^5$. In these methods, a second enzyme couples the regenerated NADH to substrate reduction. In cases where activity of two separate enzyme systems can be accomplished in vitro without undue complexity or expense, reduction of substrates with a chemical reducing agent and two enzymes can be a viable cofactor regeneration method.

Prior art attempts to electrochemically regenerate the nicotinamide cofactors avoid the need for a second enzyme, but direct electrochemical methods have typically not achieved adequate cofactor regeneration, primarily due to formation of inactive nicotinamide-dimers. The addition of certain types of electron transfer catalysts or "mediators" to electrochemical methods can greatly improve electrochemical regeneration, as disclosed by Steckhan (*Topics in Current Chemistry*, 1994, 170, 83–111). The most successful mediators are the rhodium complexes disclosed by Steckhan et al (*Ang. Chem,.* 1982, 94, 786; U.S. Pat. No. 4,526,661 and *Organometallics* 1991 10, 1568–77). Although these electrochemically-based systems have been successfully coupled to enzymatic reduction reactions, thus far cofactor turnover numbers remain too low to be commercially viable.

Photochemically assisted methods for chemical reduction of NAD(P)⁺ to NAD(P)H in the presence of similar rhodium electron transfer catalysts, and successful coupling to enzymes has been reported (Willner, et al., in *J. Am. Chem. Soc.*, 1984, 106, 5352–53, and *J. Chem. Soc., Perkin Trans.*, 2 1990, 559–64; Franke and Steckhan in *Angew. Chem. Intl. Ed. Engl.*, 1988, 27, 265; and Aono and Okura in *Inorg. Chim. Acta*, 1988, 152, 55–59). Nevertheless, an economically competitive and long-lived photo-chemical cofactor regeneration system which achieves cofactor regeneration at rates and efficiencies competitive with enzymatic methods has remained an elusive goal.

Cofactor regeneration with non-biological chemical reducing agents is a simple approach, but most chemical reducing agents are not desirably selective for production of 1,4-dihydro isomers of the cofactor nicotinamide ring, as discussed by Ohnishi and Tanimoto (*Tetrahedron Lett.* 1977, 1909–12). Dithionite salts are preferred reducing agents in this regard, providing up to about $10^2$ turnovers of the nicotinamide cofactor, as described by Jones, et al. (*J. Chem. Soc., Chem. Commun.*, 1972, 856–57). Nevertheless, dithionite salts are incompatible with many enzymes and react directly with many substrates, are expensive, and generate undesirable sulfur-containing wastes. Steckhan reported the use of formate salts to directly reduce PEG-NAD⁺ in a membrane reactor, in the presence of homogeneous rhodium catalysts having covalently bound polyethyleneglycol tails (*Angew. Chem.*, 1990, 102, 445–7). Keinan, et al. (*J. Am. Chem. Soc.* 1986, 108, 162–9) reported the use of hydride donor alcohols (such as isopropanol) and an alcohol dehydrogenase from *T. brockii*, in a "coupled substrate" method to reduce certain organic substrates. In the "coupled substrate" method one enzyme catalyzes both (a) reduction of NADP⁺ to NADPH by the hydride donor alcohol, and (b) reduction of ketone substrates such as 2-heptanone by NADPH.

Dihydrogen ($H_2$), is a highly desirable chemical reducing agent. $H_2$ is a strong reducing agent, and can be inexpensively produced and stored in high purity on a large scale. $H_2$ is typically innocuous towards enzymes and cofactors, and because it is completely consumed in most reduction reactions, it leaves no residues to complicate purification or create chemical waste. Many examples are known of the use of $H_2$ as a reducing agent in the presence of transition metal catalysts (in the absence of enzymes or cofactors).

Nevertheless, the use of hydrogen as a reducing agent in conjunction with enzymes has only been possible with complex multi-step or multi-component catalyst systems that employ indirect coupling of the of $H_2$ to cofactor regeneration. Wong et al (*J. Am. Chem. Soc.* 1981, 103, 6227–8), and Otsuka, et al. (*J. Mol. Catal.* 1989, 51, 35–9), have reported the use $H_2$ and hydrogenase enzymes, which are air-sensitive and not readily available, to reduce electron receptors such as methylviologen to produce radicals. The radicals can be coupled via a second enzyme (ferredoxin reductase) to NADH regeneration. The NADH is coupled to substrate reduction via a third enzyme.

Abril and Whitesides (*J. Am. Chem. Soc.* 1982, 104, 1552–54) reported a multi-component approach in which a water soluble rhodium complex of a bidentate phosphine ligand was employed to activate $H_2$, but two other enzymes and high concentrations of a lactate/pyruvate hydrogen carrier intermediate were required for substrate reduction.

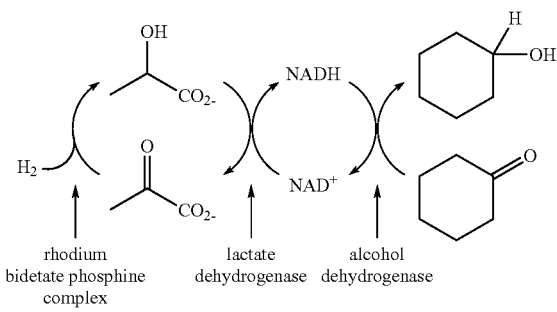

A recent report by Bhaduri, et al. (*J. Am. Chem. Soc.* 1998, 120, 12127–28) describes the use of $H_2$ to reduce $NAD^+$ to NADH via a "secondary coupling" system. $H_2$ reacts with a platinum carbonyl cluster in a methylene chloride phase and reduces a redox-active dye (Safranine O). The reduced dye then diffuses to an aqueous phase where it reduces $NAD^+$ to produce NADH. The NADH then combines with lactate dehydrogenase to reduce pyruvic acid to lactic acid. Nevertheless, the platinum carbonyl clusters are insoluble and unstable in water, necessitating the use of the redox-active dye and a two phase solvent system. No enzymes other than lactate dehydrogenase, or substrates other than pyruvic acid were reported.

Despite the potential advantages of the use of $H_2$ as a reducing agent for regenerating nicotinamide cofactors, simple, effective, and economically attractive methods for doing so have not been achieved. There is an unmet need in the art for simple and effective methods for combining the low cost and environmental desirability of $H_2$ as a reducing agent with the exquisite selectivity of enzyme catalysis. It is to such a desirable object that the present invention is primarily directed.

SUMMARY OF THE INVENTION

The present invention meets the unmet needs in the art, by providing processes and catalyst compositions, which employ $H_2$ as a reducing agent for unsaturated organic compounds in the presence of catalysts comprising enzymes.

In accordance with the purpose(s) of this invention, as embodied and broadly described herein, the invention therefore relates to, in one aspect, a process for reducing an unsaturated organic compound, comprising mixing the unsaturated organic compound and $H_2$ in the presence of a catalyst to form a reduced organic product, wherein the catalyst comprises:
  a) at least one metal salt or complex,
  b) at least one nicotinamide cofactor; and
  c) a nicotinamide cofactor dependent enzyme,
  wherein:
    i) when the metal salt or complex is a platinum carbonyl cluster complex, the catalyst does not comprise a redox active dye; and
    ii) when the metal salt or complex is a rhodium phosphine complex, the nicotinamide cofactor dependent enzyme is not a mixture of horse liver alcohol dehydrogenase and lactate dehydrogenase.

In another aspect, the invention provides a process for reducing an unsaturated organic compound, comprising mixing the unsaturated organic compound and $H_2$ in the presence of a catalyst to form a reduced organic product, wherein the catalyst comprises:
  a) a substantially aqueous buffer solution having a pH from about 6.5 to about 9.0,
  b) a water-soluble metal salt or complex comprising iron, ruthenium, osmium, cobalt, rhodium, iridium, nickel, palladium, or copper,
  c) a nicotinamide cofactor comprising $NAD^+$, NADH, $NADP^+$, NADPH, or a mixture thereof; and
  d) one nicotinamide cofactor dependent enzyme classified under the EC system as an 1.x.1.y. class enzyme, wherein x is 1,3,4, 5 or 10.

In a different aspect, the invention provides a process for reducing an unsaturated organic compound, comprising:
  a) contacting $H_2$ and a catalyst, and
  b) contacting an unsaturated organic compound with the catalyst to form a reduced organic product,
  wherein the catalyst comprises:
    i) at least one metal salt or complex,
    ii) at least one nicotinamide cofactor; and
    iii) a nicotinamide cofactor dependent enzyme,
  and wherein
    iv) when the metal salt or complex is a platinum carbonyl cluster complex, the catalyst does not comprise a redox active dye; and
    v) when the metal salt or complex is a rhodium phosphine complex, the nicotinamide cofactor dependent enzyme is not a mixture of horse liver alcohol dehydrogenase and lactate dehydrogenase.

In yet another aspect, the invention provides a process for reducing an unsaturated organic compound, comprising:
  a) contacting $H_2$, at least one metal salt or complex, and at least one nicotinamide cofactor to form at least some reduced nicotinamide cofactor, and
  b) contacting the reduced nicotinamide cofactor, a nicotinamide cofactor dependent enzyme, and an unsaturated organic compound under conditions effective to form at least some of a reduced organic product,
  wherein
    i) when the metal salt or complex is a platinum carbonyl cluster complex, the catalyst does not comprise a redox active dye; and
    ii) when the metal salt or complex is a rhodium phosphine complex, the nicotinamide cofactor dependent enzyme is not a mixture of horse liver alcohol dehydrogenase and lactate dehydrogenase.

The invention further relates to a process comprising adding dihydrogen, $H_2$, to an unsaturated organic substrate using as a catalyst a mixture comprising an enzyme, a nicotinamide cofactor, a metal salt or complex and optionally ligands, wherein the metal of the metal salt or complex is selected from iron, cobalt, nickel, copper, ruthenium, palladium, osmium, and iridium.

The invention also relates to a composition for reducing unsaturated organic compounds comprising $H_2$ and a catalyst, the catalyst comprising:
  a) at least one metal salt or complex,
  b) at least one nicotinamide cofactor; and
  c) a nicotinamide cofactor dependent enzyme,
  wherein
    i) when the metal salt or complex is a platinum carbonyl cluster complex, the catalyst does not comprise a redox active dye; and
    ii) when the metal salt or complex is a rhodium phosphine complex, the nicotinamide cofactor dependent enzyme is not a mixture of horse liver alcohol dehydrogenase and lactate dehydrogenase.

In another embodiment, the invention relates to a process for stabilizing the activity of an oxidoreductase enzyme, comprising mixing a phosphine or phosphite with an oxidoreductase enzyme.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE PREFERRED EMBODIMENTS

The present invention may be understood more readily by reference to the following detailed description of preferred embodiments of the invention and the Examples included therein and to the Figures and their previous and following description. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims that follow, reference will be made to a number of terms that shall be defined to have the following meanings:

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— repeat units in the polyester, regardless of whether ethylene glycol is used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl where there is substitution.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

In one aspect, the invention provides a process for reducing an unsaturated organic compound, comprising mixing the unsaturated organic compound and $H_2$ in the presence of a catalyst to form a reduced organic product, wherein the catalyst comprises:

a) at least one metal salt or complex,
b) at least one nicotinamide cofactor; and
c) a nicotinamide cofactor dependent enzyme.

In additional embodiments of the invention, one or more of the following further exclusions and/or limitations to the scope may apply:

a) the catalyst comprises one and only one enzyme,
b) the metal salt or complex does not comprise a platinum carbonyl cluster complex,
c) the metal salt or complex does not comprise a rhodium phosphine complex, and/or
d) the formation of the reduced organic product is capable of occurring in the absence of electrochemical or photochemical sources of external energy.

It is intended that when it is stated that the catalyst comprises "one" enzyme, one, and only one, enzyme is present in the catalyst.

Platinum carbonyl cluster complexes are metal salts or complexes having three or more platinum atoms, wherein each platinum atom is bonded to at least one carbon monoxide ligand. Examples of common platinum carbonyl complexes include but are not limited to $[Pt_9(CO)_{18}]^{2-}$, and $[Pt_{12}(CO)_{24}]^{2-}$.

When the metal salt or complex is a platinum carbonyl cluster complex; one or more of the following further exclusions and/or limitations may apply:

a) the catalyst does not comprise a redox active dye, redox active dyes including but not being limited to Safranine O, methyl viologen, methylene blue, or the like,
b) the unsaturated organic substrate is not a pyruvate,
c) the reduced organic product is not a lactate,
d) the enzyme does not comprise lactate dehydrogenase, or
e) the process does not comprise water-immiscible solvents, which include but are not limited to methylene chloride, chloroform, and the like.

Rhodium phosphine complexes are metal salts or complexes having a rhodium atom bonded to a phosphine residue, the phosphine residue having the formula $PR_3$, wherein the three R groups independently comprise hydrocarbyl groups or residues. In other embodiments, the metal salt or complex does not comprise a rhodium bis(phosphine) complex. Rhodium bis(phosphine) complexes have a rhodium atom bonded to two phosphine residues, that may or may not be bonded to each other through a bridging group, to form a bidentate phosphine ligand. In some embodiments, the metal salts or complexes do not comprise a water soluble rhodium phosphine complex.

When the metal salt or complex is a rhodium phosphine complex, one or more of the following further exclusions and/or limitations to the scope of certain embodiments of the present invention may apply:
a) the nicotinamide cofactor dependent enzyme is not lactate dehydrogenase,
b) the nicotinamide cofactor dependent enzyme is not horse liver alcohol dehydrogenase,
c) the process does not comprise lactate or pyruvate, and/or
d) the unsaturated organic substrate does not comprise cyclohexanone or 2-norbornanone.

In preferred embodiments of the processes of the current invention, the formation of the reduced organic product is capable of occurring in the absence of electrochemical or photochemical sources of external energy. In other words, the preferred processes of the present invention only require thermal energy to successfully reduce unsaturated organic compounds with $H_2$, and they do not require the presence or supply of visible or ultraviolet light, or the presence or supply of surfaces or electrodes supplied with electromotive force differentials in order to induce the formation of reduced organic products. More particularly, preferred embodiments of the present invention do not require the presence or supply of light, or the presence or supply of surfaces or electrodes supplied with electromotive force differentials to initiate the reaction of $H_2$ with the metal salt or complex component of the catalyst.

The order of mixing of the $H_2$, the unsaturated organic compound, the metal salt or complex, the nicotinamide cofactor, and the nicotinamide cofactor dependent enzyme may occur in any order, or simultaneously.

In a preferred embodiment, the invention provides a process for reducing an unsaturated organic compound, comprising mixing the unsaturated organic compound and $H_2$ in the presence of a catalyst to form a reduced organic product, wherein the catalyst comprises:
a) at least one metal salt or complex,
b) at least one nicotinamide cofactor; and
c) a nicotinamide cofactor dependent enzyme, wherein:
  i) when the metal salt or complex is a platinum carbonyl cluster complex, the catalyst does not comprise a redox active dye; and
  ii) when the metal salt or complex is a rhodium phosphine complex, the nicotinamide cofactor dependent enzyme is not a mixture of horse liver alcohol dehydrogenase and lactate dehydrogenase.

The unsaturated organic compounds of the invention are carbon containing molecules that have at least one multiple bond between two atoms of the compound, X and Y. The atoms X and Y may be any atom of the Periodic Table capable of forming multiple bonds. Preferably, the X and Y atoms are independently selected from carbon, nitrogen, oxygen, sulfur, and phosphorus atoms. Preferably, at least one of the X or Y atoms is a carbon atom. In many preferred embodiments, one of the X or Y atoms is a carbon atom, and the other atom is carbon, oxygen or nitrogen atom. Preferably, the multiple bond between the atoms X and Y is a double bond, or a triple bond. The unsaturated organic compounds can have more than one multiple bond, and the multiple bonds may form conjugated combinations of multiple bonds.

Examples of classes of unsaturated organic compounds of the invention include but are not limited to
a) a ketone, an aldehyde, a carboxylic acid, a carboxylic acid ester, or an amide,
b) an α-β unsaturated derivative of a ketone, an aldehyde, a carboxylic acid, a carboxylic acid ester, or an amide,
c) a fatty acid, a monoglyceride, a diglyceride, or a triglyceride, having an olefinic unsaturated group,
d) an olefin, an aromatic compound or a heteroaromatic compound,
e) an imine, or an oxime,
f) a sugar, an amino acid, a peptide, or a protein, wherein the sugar, amino acid, peptide, or protein has an unsaturated group.

Examples of unsaturated organic compounds include but are not limited to acetoin, 1,1-dimethoxyacetone, glycerone, acetophenone, 2-acetylfuran, hydroxy-acetone, 6-methyl-5-heptene-2-one, 5-norbornene-2-one, 2-heptanone, 8-oxo-2-nonanone, cyclopropyl methyl ketone, L-sorbose, 2,4,6/3,5-pentahydroxycyclohex-anone, aldose, glyoxylate, pyruvate, acetoacetate, ethyl 4-chloroacetoacetate, ethyl 4-oxo-hexanoate, oxaloacetate, 2,5-diketo-D-gluconic acid, D-glucono-1,5-lactone, 5α-androstane-3,17-dione, androst-4-ene-3,17-dione, L lactaldehyde, fructose, D-glyceraldehyde, orotate, 2-oxoglutarate, 3-hydroxypyruvate, glyoxylate, and L-lysine.

The reduced organic products of the invention typically correspond in structure to the starting unsaturated organic compound reduced, or a residue thereof, in which the multiple bond between the X and Y atoms is cleaved in a reduction process. Reduction is broadly defined for the purposes of this disclosure as the addition of one or more electrons to the multiple bond, the electrons having been donated by another compound, termed a reducing agent. Rearrangement and/or cleavage of functional groups may also occur during or subsequent to the reduction of the multiple bond. Often, reduction of the multiple bond is accompanied by the bonding of one or more hydrogen atoms to at least one of the X and Y atoms.

In preferred embodiments, the unsaturated organic compound comprises a carbon atom doubly bonded to another carbon, oxygen, or nitrogen atom, the reducing agent is $H_2$, and the reduced organic compound has a structure corresponding to the addition of two hydrogen atoms to the double bond, as illustrated below, in which case the reduction reaction may also be termed a hydrogenation reaction.

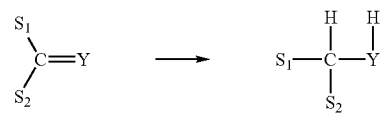

If the S1, S2 groups and/or Y groups illustrated in the equation above are different, reduction and formation of the new carbon-hydrogen bond can result in the formation of two enantiomeric isomers of the reduced organic product. The catalysts of the invention, which comprise enzymes, often selectively produce only one of the two possible enantiomeric isomers.

The processes of the invention occur in the presence of a catalyst comprising at least the following components:
a) at least one metal salt or complex,
b) at least one nicotinamide cofactor; and
c) a nicotinamide cofactor dependent enzyme.

The components of the catalyst need not, but often do comprise a single phase or mixture, so long as the component can interact in a suitable manner. The components of the catalysts can be dissolved in one or more solvents, or can be dispersed upon or bonded to one or more support phases.

In preferred embodiments of the invention, the three components of the catalyst comprise a mixture that is dispersed or substantially dissolved in a liquid medium. Preferably, the liquid medium comprises a homogeneous liquid phase. The liquid medium may comprise an organic solvent, water, or a mixture thereof. Preferably, the liquid medium comprises a substantially aqueous phase. In many preferred embodiments, the liquid medium comprises an aqueous buffer solution having a pH from about 6.5 to about 9.0, which typically maximizes the stability of the nicotinamde cofactor dependent enzymes and the nicotinamide cofactors. More preferably, the pH of the aqueous buffer solution is between about 7.0 to about 8.5. Aqueous buffer solutions comprising phosphate salts are preferred aqueous buffer solutions.

The nicotinamide cofactors employed in the invention include the naturally occurring nicotinamide adenine dinucleotides described hereinabove, and further include any structural analogs thereof that are capable of effectively interacting with the nicotinamide cofactor dependent enzymes of the invention to reduce unsaturated organic compounds. Structural analogs of the naturally occurring cofactors comprise compounds wherein the naturally occurring structure is modified by the addition of or removal of one or more functional groups. Preferably, the nicotinamide cofactors of the invention are the biologically preferred cofactors $NAD^+$, NADH, $NADP^+$, NADPH, or a mixture thereof. It is well known many nicotinamide cofactor dependent enzyme will preferentially bind and/or utilize only specifically phosphorylated cofactors (such as $NADP^+$, and NADPH), while other nicotinamide cofactor dependent enzyme will preferentially bind and/or utilize only bind and/or utilize non-phosphorylated cofactors (such as $NAD^+$, NADH).

The nicotinamide cofactor dependent enzymes employed in the invention comprise any naturally occurring or biotechnologically modified or engineered enzyme that requires the presence of a nicotinamide cofactor, or an analog thereof, in order to reduce or oxidize organic substrates. It is to be understood that while many nicotinamide cofactor dependent enzymes catalyze oxidation reactions in nature, they are nevertheless often useful for catalyzing the reduction processes of the invention.

The Enzyme Commission of International Union of Biochemistry and Molecular Biology ("EC") has devised a well-known four digit numerical system for classifying enzymes, in terms of the type of reaction that the enzymes catalyze. The EC classification system has been described by Dixon, Webb, Thorne, and Tipton ("Enzymes", Chapter 5, pages 207–230, Academic Press, 1979), which is hereby incorporated by reference in its entirety, for the purposes of describing the classification of enzymes and the relationship of the classifications to the substrates and products of the reactions catalyzed by the enzymes.

The first digit of an Enzyme Classification ("EC") corresponds to one of six classes of enzymes. The nicotinamide cofactor dependent enzymes of the present invention are all members of the class of oxidoreductases, which comprise enzymes that mediate the transfer of electrons, H atoms, or hydride atoms. Oxidoreductases all have a first digit EC classification of "1".

The second digit of an EC classification relates to sub-classes of the enzymes specified by the first digit. For an oxidoreductase, the second digit pertains to a group of twenty subclasses of functional groups of the substrates and/or products for the enzyme, i.e. classes of the functional groups in the substrates or products which undergo oxidation or reduction. The third digit of an EC classification relates to another series of sub-subclasses. In the case of the oxidoreductases, a third digit of "1" indicates an oxidoreductase that requires the presence of nicotinamide cofactors. Therefore, the nicotinamide cofactor dependent enzymes of the present invention are all classified under the EC system as "1.x.1.y." class enzymes. The fourth digit of and EC classification specifies a serial number for the enzyme, which is often related to the particular identity of the natural substrate of the enzyme.

Preferred embodiments of the invention employ nicotinamide cofactor dependent enzymes, which may be further defined by the values of x and y in the EC classification of the enzyme. The second digit of an EC classification of an enzyme, i.e., the value of x, corresponds to the class of functional group oxidized or reduced by the enzyme. Preferred enzymes of the invention have x values of 1, 3, 4, 5, or 10, corresponding to ketone or aldehyde reductions (x=1); olefin reduction (x=3); imine reductions (x=4 or 5); and reduction of diphenols or ascorbate (x=10). Therefore in preferred embodiments of the present invention, the nicotinamide cofactor dependent enzyme is an enzyme classified under the EC system as an 1.x.1.y. class enzyme, wherein x is 1,3,4,5 or 10. More than 340 enzymes are presently known to fall within those preferred classes of enzymes.

For enzymes within the class of 1.1.1.y enzymes, Table 1 below relates the value of y to the name of the enzyme and its natural substrates.

TABLE 1

| 1.1.1.y Class Enzymes. | |
| --- | --- |
| y | Name of Enzyme |
| 1 | alcohol dehydrogenase |
| 2 | alcohol dehydrogenase |
| 4 | butanediol dehydrogenase |
| 5 | diacetyl reductase |
| 6 | glycerol dehydrogenase |
| 7 | glyerol-3-phosphate dehydrogenase |
| 14 | L-iditol 2-dehydrogenase |
| 18 | myo-inositol 2-dehydrogenase |
| 21 | aldose reductase |
| 22 | UDP glucose 6-dehydrogenase |
| 26 | glyoxalate dehydrogenase |
| 27 | L-lactate dehydrogenase |
| 30 | 3-hydroxybutyrate dehydrogenase |
| 37 | malate dehydrogenase |
| 40 | malate dehydrogenase |
| 41 | isocitrate dehydrogenase |
| 42 | isocitrate dehydrogenase |
| 44 | phosphogluconate dehydrogenase |
| 47 | glucose 1-dehydrogenase |
| 48 | galactose 1-dehydrogenase |
| 49 | glucose-6-phosphate 1-dehydrogenase |
| 50 | 3a-hydroxysteroid dehydrogenase |
| 51 | 3 (or 17) b-hydroxysteroid dehydrogenase |
| 53 | 3a (or 20b) hydroxysteroid dehydrogenase |
| 55 | lactaldehyde reductase |
| 67 | mannitol 2-dehydrogenase |
| 72 | glycerol dehydrogenase |
| 83 | D-malate dehydrogenase |
| 95 | glycerol dehydrogenase |
| 119 | glucose 1-dehydrogenase |
| 122 | D-threo-aldose 1-dehydrogenase |
| 159 | 12a-hydroxysteroid dehydrogenase |
| 176 | 12a-hydroxysteroid dehydrogenase |

For enzymes within the class of 1.3.1.y enzymes, enzymes of class 1.3.1.14 i.e. orotate reductases are preferred. (NADH)

For enzymes within the class of 1.4.1.y enzymes, Table 2 below relates the value of y to the name of the enzyme and/or it's natural substrate.

TABLE 2

1.4.1.y Class Enzymes.

| y | Name of Enzyme |
|---|---|
| 1 | alanine dehydrogenase |
| 2 | glutamate dehydrogenase |
| 3 | glutamate dehydrogenase |
| 4 | glutamate dehydrogenase |
| 5 | L-amino-acid dehydrogenase |
| 7 | serine dehydrogenase |
| 8 | valine dehydrogenase |
| 9 | leucine dehydrogenase |
| 10 | glycine dehydrogenase |
| 11 | L-erythro-3,5-diaminohexanoate dehydrogenase |
| 12 | 2,4-diaminopentanoate dehydrogenase |
| 13 | glutamate synthase |
| 14 | glutamate synthase |
| 15 | lysine dehydrogenase |
| 16 | diaminopimelate dehydrogenase |
| 17 | N-methylalanine dehydrogenase |
| 18 | lysine 6-dehydrogenase |
| 19 | tryptophane dehydrogenase |
| 20 | phenylalanine dehydrogenase |

In preferred embodiments of the invention, the nicotinamide cofactor dependent enzyme is an enzyme classified under the EC system as a 1.1.1.1, a 1.1.1.2, a 1.1.1.4, a 1.1.1.5, a 1.1.1.6, a 1.1.1.7, a 1.1.1.14, a 1.1.1.18, a 1.1.1.21, a 1.1.1.22, a 1.1.1.26, a 1.1.1.27, a 1.1.1.30, a 1.1.1.37, a 1.1.1.40, a 1.1.1.41, a 1.1.1.42, a 1.1.1.44, a 1.1.1.47, a 1.1.1.48, a 1.1.1.49, a 1.1.1.50, a 1.1.1.51, a 1.1.1.53, a 1.1.1.55, a 1.1.1.67, a 1.1.1.72, a 1.1.1.83, a 1.1.1.95, a 1.1.1.119, a 1.1.1.122, a 1.1.1.159, a 1.1.1.176, a 1.3.1.14, a 1.4.1.1, a 1.4.1.2, a 1.4.1.3, a 1.4.1.4, a 1.4.1.5, a 1.4.1.7, a 1.4.1.8, a 1.4.1.9, a 1.4.1.10, a 1.4.1.11, a 1.4.1.12, a 1.4.1.13, a 1.4.1.14, a 1.4.1.15, a 1.4.1.16, a 1.4.1.17, a 1.4.1.18, a 1.4.1.19 or a 1.4.1.20 class enzyme.

In more preferred embodiments of the invention, the nicotinamide cofactor dependent enzyme is an enzyme classified under the EC system as 1.1.1.1, 1.1.1.2, 1.1.1.5, 1.1.1.6, 1.1.1.7, 1.1.1.14, 1.1.1.18, 1.1.1.21, 1.1.1.26, 1.1.1.27, 1.1.1.37, 1.1.1.40, 1.1.1.41, 1.1.1.42, 1.1.1.47, 1.1.1.48, 1.1.1.49, 1.1.1.72, 1.1.1.83, 1.1.1.95, 1.1.1.119, 14, 1.4.1.1, 1.4.1.3, 1.4.1.4, 1.4.1.9 or 1.4.1.20 class enzyme.

In other preferred embodiments of the invention the nicotinamide cofactor dependent enzyme is an enzyme classified under the EC system as a 1.1.1.1 or 1.1.1.2, class enzyme.

In the present invention, the specification of an enzyme by its EC classification does not necessarily strictly limit the classes or species of unsaturated organic compounds that may be reduced by the enzyme in the processes of the invention, or the reduced organic products produced. In many embodiments of the present invention, the methods of the invention will reduce unnatural unsaturated organic compounds, to produce unnatural reduced organic products, which will not be literally specified by the EC classification of an enzyme.

Nevertheless, it is to be understood that the $2^{nd}$ and/or $4^{th}$ digits of the EC classification of a particular oxidoreductase enzyme inherently identifies preferred classes of oxidation and/or reduction reactions that may be catalyzed by the enzyme, and/or the corresponding classes and/or species of substrates and products that may be involved. A listing of the names, EC classifications and the corresponding chemical reactions of the oxidoreductase enzymes relevant to the present invention may found in "Enzyme Nomenclature 1992—Recommendations of the Nomenclature Committee of the International Union of Biochemistry and Molecular Biology on the Nomenclature and Classification of Enzymes", pages 1–154, Academic Press, 1992, which is hereby incorporated by reference, for the purposes of describing the classification of enzymes and the relationship of the classifications to the substrates and products of the reactions catalyzed by the enzymes. Of particular relevance are pages 24–55 (1.1.1.y class enzymes), pages 65–67 (1.2.1.y class enzymes), pages 76–83 (1.3.1.y class enzymes), pages 87–89 (1.4.1.y class enzymes), pages 93–96 (1.5.1.y class enzymes), and 1.13 (1.10.1.y class enzymes).

For example, if the nicotinamide cofactor dependent enzyme is an alcohol dehydrogenase [1.1.1.1] or [1.1.1.2], a preferred reduced organic product is an alcohol.

In a similar manner, preferred classes or species of reduced organic products are hereinbelow identified for a number of particular EC enzyme classifications. For example, if the nicotinamide cofactor dependent enzyme is an aldose reductase [1.1.1.21], a preferred reduced organic product is an alditol. If the nicotinamide cofactor dependent enzyme is a glyoxolate reductase [1.1.1.26], a preferred reduced organic product is a glycolate or glycerate.

With respect to the identification of preferred species of reduced organic products for particular enzymes: If the nicotinamide cofactor dependent enzyme is a diacetyl reductase [1.1.1.5], a preferred reduced organic product is 3-hydroxy-2-butanone (acetoin). If the nicotinamide cofactor dependent enzyme is a glycerol dehydrogenase [1.1.1.6], a preferred reduced organic product is glycerol. If the nicotinamide cofactor dependent enzyme is an propanediol-phosphate dehydrogenase [1.1.1.7], a preferred reduced organic product is propane-1,2-diol 1-phosphate. If the nicotinamide cofactor dependent enzyme is an L-lactate dehydrogenase [1.1.1.27], a preferred reduced organic product is an (S)-lactate. If the nicotinamide cofactor dependent enzyme is a malate dehydrogenase [1.1.1.37], a preferred reduced organic product is (S)-malate. If the nicotinamide cofactor dependent enzyme is malate dehydrogenase [1.1.1.40], a preferred reduced organic product is (S)-malate. If the nicotinamide cofactor dependent enzyme is isocitrate dehydrogenase [1.1.1.41], a preferred reduced organic product is isocitrate. If the nicotinamide cofactor dependent enzyme is isocitrate dehydrogenase [1.1.1.42], a preferred reduced organic product is isocitrate.

Moreover, if the nicotinamide cofactor dependent enzyme is glucose 1-dehydrogenase [1.1.1.47], a preferred reduced organic product is β-D-glucose. If the nicotinamide cofactor dependent enzyme is galactose 1-dehydrogenase [1.1.1.48], a preferred reduced organic product is D-galactose. If the nicotinamide cofactor dependent enzyme is glucose 6-phosphate 1-dehydrogenase [1.1.1.49], a preferred reduced organic product is D-glucose 6-phosphate. If the nicotinamide cofactor dependent enzyme is glycerol dehydrogenase (NADP) [1.1.1.72], a preferred reduced organic product is glycerol. If the nicotinamide cofactor dependent enzyme is D-malate dehydrogenase [1.1.1.83], a preferred reduced organic product is (R)-malate. If the nicotinamide cofactor dependent enzyme is phosphoglycerate dehydrogenase [1.1.1.95], a preferred reduced organic product is 3-phosphoglycerate. If the nicotinamide cofactor dependent enzyme is glucose 1-dehydrogenase (NADP) [1.1.1.119], a preferred reduced organic product is D-glucose, D-mannose, 2-deoxy-D-glucose or 2-amino-2-deoxy-D-mannose.

Additionally, if the nicotinamide cofactor dependent enzyme is alanine dehydrogenase [1.4.1.1], a preferred reduced organic product is L-alanine. If the nicotinamide cofactor dependent enzyme is glutamate dehydrogenase [1.4.1.3], a preferred reduced organic product is L-glutamate. If the nicotinamide cofactor dependent enzyme is glutamate dehydrogenase [1.4.1.4], a preferred reduced organic product is L-glutamate. If the nicotinamide cofactor dependent enzyme is leucine dehydrogenase [1.4.1.9], a preferred reduced organic product is L-leucine. If the nicotinamide cofactor dependent enzyme is phenylalanine dehydrogenase [1.4.1.20], a preferred reduced organic product is L-phenylalanine.

It is to be understood that in the preceding description relating the EC classifications of preferred enzymes to their substrates, the invention further provides methods for reducing man-made structural analogs of the natural substrates, to produce unnatural reduced organic products It has been found that the maintenance of optimal activity of the enzymes is improved in the presence of certain stabilizers. Therefore, in preferred embodiments, the processes and compositions of the invention further comprise a stabilizer for the nicotinamide cofactor dependent enzyme. Preferably the stabilizers comprise sulfur or phosphorus compounds. Preferred sulfur containing stabilizers have sulfhydril groups, and include compounds exemplified by dithiothreitol (DTT), mercaptoethanol, and the like. Preferred phosphorus containing stabilizers have phosphorus atoms with oxidizable pairs of unshared electrons, such as phosphines, or phosphites, which include compounds such as tris(m-sulfonatophenyl)phosphine trisodium salt (TPPTS), or 1,3,5-triaza-7-phosphaadamantane (PTA).

Most of the nicotinamide cofactor dependent enzymes of the invention have cysteine amino acid residues. Nevertheless, preferred nicotinamide cofactor dependent enzymes of the invention do not comprise a cysteine amino acid residue, because such enzymes may not require the presence of a stabilizer. Two cysteine-free enzymes which are preferred in the practice of the present invention are 2,5-diketo-D-gluconic acid reductase and glucose-6-phosphate and 1-dehydrogenase.

It is also to be understood that enzymes are often highly selective for the production of only one of two possible enantiomers of a reduced organic product. Therefore, in preferred embodiments, the invention provides processes wherein the reduced organic product is produced in a substantial enantiomeric excess.

The catalysts of the invention also comprise at least one metal salt or complex. The metal salt or complex may comprise any compound, composition, or phase containing at least one transition metal element, lanthanide metal element, or actinide metal element from the Periodic Table of the elements, with the proviso that the metal salt or complex is not nicotinamide cofactor dependent enzyme that contains a transition metal element, a lanthanide metal element, or an actinide metal element as part of its structure. Preferably, the metal salt or complex comprises a transition metal element selected from Groups 8, 9, 10, or 11 of the Periodic Table. Preferred elements from Groups 8, 9, 10, or 11 comprise, iron, ruthenium, osmium, cobalt, rhodium, iridium, nickel, palladium, platinum, or copper. In highly preferred embodiments of the invention, the metal salt or complex comprises ruthenium, rhodium, or palladium. The most preferred metal element is ruthenium.

The preferred oxidation state of the metal salt will vary with the identity of the metal, process variables such as the medium, the pressure of $H_2$, and the identity of any ligands bonded to the metal. It is to be understood that the oxidation state of the metal added to the mixture may be altered by the presence of the other components of the reaction. Examples of species of metal salts or complexes include but are not limited to iron trichloride, ferrocene, iron pentacarbonyl, ruthenium trichloride hydrate, $[Cl_2Ru(TPPTS)_2]_2$, osmium tetraoxide, dicobalt octacarbonyl, rhodium trichlorided, $[ClRh(P(C_6H_5)_3)_3]$, $[ClRh(TPPTS)_3]$, nickel tetracarbonyl, nickel acetate, $[Cl_2Pd(P(C_6H_5)_3)_2]$, $Na_2[PtCl_6]$, $CuBr_2$, and the like.

In many embodiments of the invention, the metal salt or complex comprises one or more ligands. Ligands are any organic or inorganic compound that can coordinately, datively, or covalently bond to the metal atom of the metal salt or complex. Examples of suitable ligands include but are not limited to water, a hydroxide, an oxide, an amine, an amide, an imine, an oxime, an imide, a nitrogen containing heterocycle, a nitrogen containing macrocycle, a nitrile, a phosphine, a phosphide, a phosphite, an alcohol, a thiol, an alcoholate, a thiolate, a sulfur containing heterocycle, an oxygen containing heterocycle, an ether, a cyclic ether, a thioether; a phenol, a thiophenol, a phenolate, a thiophenolate; a halide, a hydride, a borohydride, a ketone, an aldehyde, a carboxylic acid, an ester, an amino acid, a carboxylate, an acetonate, an iminate, an acetylacetonate, an iminoacetonate, an iminoiminate, an alkene, an alkyne, a diene, an allyl residue, a dienyl residue a cyclopentadienyl residue, an indenyl residue, an arene, a polycyclic aromatic residue, a hydrocarbyl residue, carbon monoxide, a cyanide, nitric oxide, $H_2$, substituted silyl residues, a sulfate, a sulfoxide, a sulfone, a sulfonate, a phosphate, a phosphonate, or any ligand containing more than one of the above functional groups or residues.

In preferred embodiments of the invention, the metal salt or complex has a ligand comprising a phosphine residue, a phosphite residue, carbon monoxide, a cyclopentadienyl residue, an aromatic residue, a halide, or a hydride. A phosphine residue comprises a trivalent phosphorus residue having the formula $PR_1R_2R_3$. A phosphite residue comprises a trivalent phosphorus residue having at least one alkoxy residue in substitution for the $R_1$, $R_2$, or $R_3$ residues of a phosphine. Preferably, the $R_1$, $R_2$, and $R_3$ residues of the phosphines and/or phosphites are independently selected from hydrogen, alkyl, alkylene, aryl, or halide residues.

In other preferred embodiments of the invention, the metal salt or complex has a ligand comprising a phosphine residue, a phosphite residue, a cyclopentadienyl residue, or an aromatic residue, wherein the ligand has one or more polar functional groups. Preferred polar functional groups include one or more hydroxyl, carboxylic, amine, amide, ketone, aldehyde, nitro, and other similar polar substituent groups for organic compounds. Preferred polar functional groups also include anionic groups, cationic groups, or poly(alkylene glycol) groups. Preferred anionic polar functional groups include carboxylates, sulfates, sulphonates, phosphates, phosphonates, and the like. Preferred cationic polar functional groups include ammonium groups, sulfonium groups, phosphonium groups, and the like. Preferred poly(alkylene glycol) functional groups include poly(ethylene glycol) groups, polypropylene glycol groups, polybutylene glycol groups, and the like.

Although the polar functional groups may serve various purposes, such as modification of the properties and reactivity of the metal complex, in many preferred embodiments, the polar functional group serves the purpose of increasing the water solubility of the ligand and/or the resulting metal salt or complex. A particularly preferred class of ligands are water soluble phosphine or phosphite ligands, which are useful as homogenous catalysts, as described by Kalck and Monteil (*Adv. Organomet. Chem.*, 1992, 34, 219–284). A preferred class of water soluble phosphine ligands comprises phosphine compounds having one or more anionic sulfonate groups. A well known example of such compounds comprises a salt of tris(m-sulfonatophenyl)phosphine. Another known water soluble phosphine ligand is 1,3,5-triaza-7-phosphaadamantane, as described by. Daigle et al. (*Inorg. Synth.*, 1998, 32, 40–45).

Preferred metal salts or complexes are significantly soluble in water. Significant water solubility permits the metal salt or complex to react with and/or activate $H_2$ in the water phase, and rapid transfer of hydrogen to reduce the water soluble nicotinamide cofactors. Metal salts or complexes are significantly soluble in water if the metal of the metal salt or complex is solubilized to the extent of at least about 1 part per million in water. Preferably, the metal is soluble to the extent of greater than about 10 parts per million in water. Even more preferably, the metal is soluble to the extent of greater than about 100 parts per million in water.

$H_2$, i.e. dihydrogen, is the reducing agent supplied to the processes of the invention. $H_2$ has very significant practical and environmental advantages as compared with other chemical reducing agents, as discussed hereinabove. $H_2$ is also very economically attractive from a cost perspective. The table below illustrates the relative costs of a series of relevant reducing agents.

TABLE 3

Cost of One Mole of Various "Hydride Reagents"

| Reducing Agent | mol wt. | $/mole |
| --- | --- | --- |
| $H_2$ | 2 | 0.01[a] |
| glucose | 180 | 0.24[b] |
| $Na[CO_2H]$ | 68 | 3[b] |
| $NaBH_4$ | 38 | 32[b] |
| NADH | 709 | 26,781[c] |
| NADPH | 833 | 358,190[c] |

[a]Chemical Market Reporter
[b]Aldrich Catalog
[c]Sigma Catalog

The $H_2$ may be present at any pressure which is effective to produce at least some of the reduced organic product. The pressure of $H_2$ that will produce at least some reduced organic product will vary with the compositions of the catalyst, the reaction temperature, and other reaction conditions, and variables. Preferably the $H_2$ is present at a pressure less than about 100 atmospheres. More preferably, the $H_2$ is present at a pressure from about 0.1 atmospheres to about 50 atmospheres. Even more preferably, the $H_2$ is present at a pressure from about 1 atmosphere to about 20 atmospheres.

The processes of the invention can occur at any temperature that induces the reduction of the unsaturated organic compounds, while not substantially denaturing the activity of the nicotinamide enzyme, or substantially deactivating the nicotinamide cofactors. Preferably, the processes of the invention are conducted at a temperature from about 0° C. to about 90° C. More preferably, the processes of the invention are conducted at a temperature from about 0° C. to about 45° C.

In a preferred embodiment, the invention provides a process for reducing an unsaturated organic compound, comprising mixing the unsaturated organic compound and $H_2$ in the presence of a catalyst to form a reduced organic product, wherein the catalyst comprises:

a) a substantially aqueous buffer solution having a pH from about 6.5 to about 9.0, b) a water-soluble metal salt or complex comprising iron, ruthenium, osmium, cobalt, rhodium, iridium, nickel, palladium, or copper, c) a nicotinamide cofactor comprising $NAD^+$, NADH, $NADP^+$, NADPH, or a mixture thereof; and d) one nicotinamide cofactor dependent enzyme classified under the EC system as an 1.x.1.y. class enzyme, wherein x is 1,3,4, 5 or 10.

In another preferred embodiment, the invention provides a process comprising adding dihydrogen, $H_2$, to an unsaturated organic substrate using as a catalyst a mixture comprising an enzyme, a nicotinamide cofactor, a metal salt or complex and optionally ligands, wherein the metal of the metal salt or complex is selected from iron, cobalt, nickel, copper, ruthenium, palladium, osmium, iridium. In even more preferred embodiments, the metal of the metal salt or complex is selected from ruthenium and palladium.

It is clear that in the absence of a catalyst, the unsaturated organic compounds of the reaction typically do not react with $H_2$, and are not reduced by $H_2$ to form the reduced organic products of the invention. Therefore, the invention provides a preferred process for reducing an unsaturated organic compound, comprising:

a) contacting $H_2$ and a catalyst, and b) contacting an unsaturated organic compound with the catalyst to form a reduced organic product, wherein the catalyst comprises:

i) at least one metal salt or complex, ii) at least one nicotinamide cofactor; and iii) a nicotinamide cofactor dependent enzyme, and wherein iv) when the metal salt or complex is a platinum carbonyl cluster complex, the catalyst does not comprise a redox active dye; and v) when the metal salt or complex is a rhodium phosphine complex, the nicotinamide cofactor dependent enzyme is not a mixture of horse liver alcohol dehydrogenase and lactate dehydrogenase.

It is to be understood that in the embodiments of the invention described immediately above, $H_2$, the catalyst, and the unsaturated organic compound may all be present in a mixture or single phase, but it is not necessary that the unsaturated organic product is directly contacted with $H_2$. In some embodiments, the catalyst (or certain components thereof) might be contacted with $H_2$ in one reaction phase or reactor, while the unsaturated organic product was contacted with catalyst in a different phase or reactor. The steps of contacting $H_2$ and a catalyst, and contacting an unsaturated organic compound with the catalyst may occur simultaneously, or sequentially.

Furthermore, in an alternative but similar embodiment, the invention provides a process for reducing an unsaturated organic compound, comprising:

a) contacting $H_2$, at least one metal salt or complex, and at least one nicotinamide cofactor to form at least some reduced nicotinamide cofactor, and b) contacting the reduced nicotinamide cofactor, a nicotinamide cofactor dependent enzyme, and an unsaturated organic compound under conditions effective to form at least some of the reduced organic product, wherein i) when the metal salt or complex is a platinum carbonyl cluster complex, the catalyst does not comprise a redox active dye; and ii) when the metal salt or complex is a rhodium phosphine complex, the nicotinamide cofactor dependent enzyme is not a mixture of horse liver alcohol dehydrogenase and lactate dehydrogenase.

In the embodiment described immediately above, the contacting steps may occur simultaneously, or sequentially; the reaction steps may also occur in the same phase or reactor. Alternatively, the metal salt or complex, and the nicotinamide cofactor might be contacted with $H_2$ in one reaction phase or reactor, while the unsaturated organic product was contacted with enzyme and the reduced organic cofactor in a different phase or reactor.

In preferred embodiments of step a) of the process described immediately above, the $H_2$ reacts with the metal salt or complex to form at least some of a metal hydrogen complex, and the metal hydrogen complex reacts directly with the nicotinamide cofactor to transfer hydrogen from the metal hydrogen complex to the nicotinamide cofactor.

In yet another aspect, the current invention provides a composition for reducing unsaturated organic compounds comprising $H_2$ and a catalyst, the catalyst comprising:
 a) at least one metal salt or complex,
 b) at least one nicotinamide cofactor; and
 c) a nicotinamide cofactor dependent enzyme,
 wherein
  i) when the metal salt or complex is a platinum carbonyl cluster complex, the catalyst does not comprise a redox active dye; and
  ii) when the metal salt or complex is a rhodium phosphine complex, the nicotinamide cofactor dependent enzyme is not a mixture of horse liver alcohol dehydrogenase and lactate dehydrogenase.

As previously described hereinabove, many embodiments of the above-described processes for reducing unsaturated organic compounds with $H_2$ employ oxidoreductase enzymes whose activity is enhanced or maintained by the presence of certain stabilizers. It is known in the art to employ certain sulfur containing stabilizers, and in particular it is known in the art to employ stabilizers having sulfhydril groups, which are exemplified by compounds such as dithiothreitol (DTT), mercaptoethanol, and the like.

Unexpectedly, it has been discovered that certain phosphorus containing compounds can also stabilize oxidoreductase enzymes. The enzyme stabilization occurs independently of the presence or absence of the $H_2$, or unsaturated organic compounds employed in the processes described above. In particular, it has been unexpectedly discovered that phosphines or phosphites can stabilize oxidoreductase enzymes in a variety of processes.

Therefore, in one aspect the invention provides a process for stabilizing the activity of an oxidoreductase enzyme, comprising mixing a phosphine or phosphite with an oxidoreductase enzyme. In preferred embodiments of the invention, the mixing of the phosphine or phosphite with the oxidoreductase enzyme occurs in a liquid medium. The liquid medium may comprise water, an organic solvent, or a mixture thereof. Preferably, the liquid medium comprises a substantially aqueous buffer solution.

Preferably, the mixing of the phosphine or phosphite with the oxidoreductase enzyme is effective to slow the loss of activity of the oxidoreductase enzyme, as compared to the rate of loss of activity of the oxidoreductase enzyme in the absence of the phosphine or phosphite. While not wishing to be bound by theory, it is believed that the phosphine or phosphite compounds serve as reducing agents for certain oxidation sensitive components of the enzymes, including cysteine amino acid residues contained in the enzymes.

Preferably, the phosphine or the phosphite comprise phosphorus derivatives $PR_n(O-R)_{3-n}$, wherein n is an integer of from zero to three. Preferably, the R groups comprise from 1 to about 10 carbon atoms. The R groups (whether bonded to phosphorus or oxygen) are independently selected, and may be the same or different. Preferably, the R groups are hydrocarbyl, or substituted hydrocarbyl, groups, which include alkyl, cycloakyl, aromatic and heteroaromatic groups.

Preferably, one or more of the R groups is substituted with one or more polar groups. Preferred polar groups include salts of anionic groups such as sulfonate, and carboxylate groups; salts of cationic groups such as alkylammonium groups, or polar but electrically neutral groups such as hydroxyl, amino, alcohol, or polyalkylene glycol groups. Polyethylene glycol groups are preferred polyalkylene glycol groups. The polar groups are believed to be beneficial in improving the effectiveness of the phosphine or phosphite stabilizers because the polar groups tend to increase the water solubility of the phosphines or phosphites, so that they can more effectively interact with the oxidoreductase enzymes, which are also water soluble.

Experimental

The following examples are put forth so as to provide those of ordinary skill in the art with a complete disclosure and description of how the compounds, and associated processes and methods are constructed, used, and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. (Celsius) or is at ambient temperature, and pressure is at or near atmospheric.

Materials and Methods

Tris(m-sulfonatophenyl)phosphine trisodium salt (TPPTS) was purchased from Strem Chemical and sodium diphenylphosphinobenzene-3-sulfonate (TPPMS) from TCI America. Alcohol dehydrogenase enzymes of *Thermanaerobium brockii* (TBADH, EC 1.1.1.2), β-nicotinamide adenine dinucleotide ($NAD^+$), β-nicotinamide adenine dinucleotide phosphate ($NADP^+$) and their respective reduced forms were purchased from Sigma Chemical and stored in a refrigerator (−10° C.). The preparation of TBADH is described in U.S. Pat. No. 4,352,885. $RuCl_3$-hydrate (38.4% Ru) was obtained from Colonial Metals, Inc. 1,3,5-Triaza-7-phosphaadamantane (PTA) was prepared by the procedure of Daigle, et al. (*Inorg. Synth.* 1998, 32, 40–45). $[Cl_2Ru(TPPTS)_2]_2$ was prepared by the procedure of Hernandez, and Kalck (*J. Mol. Catal. A. Chem.*, 1993, 116, 117–130). $Cl_2Ru(PTA)_4$ was prepared by the procedure of Darensbourg, et al., (*Inorg. Chem.*, 1994, 33, 200–08). Phosphate buffer was prepared using $KHPO_4$. Procedures for 2-heptanone reduction using isopropanol to regenerate NADP were adapted from Keinan, et al. (*J. Am. Chem. Soc.* 1986, 108, 162). $^1H$ and $^{13}C$ NMR spectra were recorded on a Varian Gemini-300 spectrometer. Reference samples of $NAD^+$, NADH, $NADP^+$ and NADPH were dissolved in $D_2O$ and their chemical shifts (δ) are reported relative to sodium 3-(trimethylsilyl)propionate (TMSP). Chemical shift assignments have been made in accord with Ragg, et al. (*J. Biochim. Biophys. Acta* 1991, 1076, 49) and Oppenheimer (*Proc. Natl. Acad. Sci. U.S.* 1971, 68, 3200). GLC was conducted on a HP 6890 gas chromatograph with a 30' DB-FFAP capillary column and flame ionization detection. Samples of (R)-(−)-2-heptanol (95%) and (S)-(+)-2-heptanol (99%, 97% ee) were obtained from Aldrich Chemical.

Samples were analyzed by conversion to their trifluoroacetate esters by a standardized treatment with trifluoroacetic anhydride. The enantiomeric excess of (S)-2-heptanol produced by enzymatic reduction was determined by chiral GC and comparison to (R)- and (S)-2-heptanol standards using a Cyclodex-B column (30 m ×0.25, 0.25µ film) at 40° C. Under these conditions the retention times of the trifluoroacetates of (R)-2-heptanol and (S)-2-heptanol were 28.15 minutes and 28.77 minutes.

EXAMPLE 1

Example 1 demonstrates that $H_2$ can be used to convert 2-butanone to 2-butanol in the presence of a catalyst comprising a ruthenium complex, TBADH and $NADP^+$.

$NADP^+$ (28.0 mg, 36.6 µmol) was placed in 2 mL of a 0.1 M phosphate buffer and the pH adjusted to 8.1 with NaOH. TBADH (1.2 mg, 8.8 units) was added to this solution and it was placed in an 80 mL Fisher-Porter bottle. The Fisher-Porter bottle was evacuated and refilled with argon three times then $[Cl_2Ru(TPPTS)_2]_2$ (6.4 mg, 5.0 µmol) and 2-butanone (5 µl) were added under a flow of argon. The Fisher-Porter bottle was evacuated and filled with 70 psi of $H_2$ and heated to 40° C. for 2.0 hr. The pressure was released from the bottle and a liquid sample analyzed by GLC showed the production of 9.6 µmol of 2-butanol.

Comparative Example 1a

Comparative Example 1a demonstrates that without the enzyme (TBADH) the conditions applied in Example 1 produce no reaction.

$NADP^+$ (39.0 mg, 51.5 µmol) was placed in 2 mL of a 0.1 M phosphate buffer. The pH of this solution was adjusted to 8.1 with NaOH and then placed in an 80 mL Fisher-Porter bottle. The Fisher-Porter bottle was evacuated and refilled with argon three times then $[Cl_2Ru(TPPTS)_2]_2$ (8.8 mg, 6.9 µmol) and 2-butanone (10 µl) were added under a flow of argon. The Fisher-Porter bottle was evacuated and filled with 70 psi of $H_2$ and heated to 40° C. for 2.0 hr. The pressure was released from the bottle and a liquid sample analyzed by GLC showed the production of no 2-butanol. The reaction solution was stripped to dryness under reduced pressure and the residue was dissolved in $D_2O$. $^1H$ NMR analysis showed that only a trace of $NADP^+$ remained and that NADPH was the dominant species remaining.

EXAMPLE 2

Example 2 demonstrates that $H_2$ can be used to convert 2-heptanone to 2-heptanol in significant enantiomeric in the presence of a catalyst comprising a ruthenium complex, TBADH and $NADP^+$.

An 80 mL Fisher-Porter bottle with a micro-liquid sampling tube was charged with 20 mL of a 0.1 M phosphate buffer (pH=7.0), 2-heptanone (100 µl, 718 µmol), TPPTS(74 mg, 130.7 µmol), $NADP^+$ (10 mg, 13.1 µmol) and TBADH (2.7 mg, 19.8 units) under a flow of argon. Ruthenium catalyst, $[Cl_2Ru(TPPTS)_2]_2$ (17 mg, 6.5 µmol), was finally added and the Fisher-Porter bottle was sealed, evacuated and filled with 70 psi of $H_2$. Evacuation and refilling with $H_2$ were repeated two times and the apparatus was then heated to 60° C. with an oil bath. After 10 hours GC analysis of a microsample removed via the liquid sampler showed the production of 227.8 µmol of 2-heptanone. After an additional four hours an additional 13.0 µmol had accumulated (240.8 µmol). The pressure was released from the bottle and a liquid sample analyzed by chiral GC showed the 2-heptanol to be 70.5% (S) and 29.5% (R) (41.0% ee). Turnovers of catalyst components: $NADP^+_{TO}=18.4$

EXAMPLE 3

Example 3 demonstrates that the ruthenium catalyst $[Cl_2Ru(TPPTS)_2]_2$ is a catalyst precursor for the reduction of $NAD(P)^+$ with $H_2$.

$NADP^+$ (36.0 mg, 47.0 µmol) was placed in 2 mL of a 0.1 M phosphate buffer. The pH of this solution was adjusted to 8.3 with NaOH and then placed in an 80 mL Fisher-Porter bottle. The Fisher-Porter bottle was evacuated and refilled with argon three times then $[Cl_2Ru(TPPTS)_2]_2$ (9.7 mg, 3.7 µmol) was added under a flow of argon. The Fisher-Porter bottle was evacuated and filled with 70 psi of $H_2$ and heated to 40° C. for 3.0 hr. The volatiles were removed under reduced pressure and a sample dissolved in $D_2O$. To this was added 20 µl of trimethylsilylpropionate standard solution. $^1H$ NMR integration shows that 29.0 µmole of NADPH have been produced under these conditions.

$NADP^+$
$^1H$ ($D_2O$): δ 9.35 (s) $N_2$, 9.17 (d, 0.6 Hz) $N_6$, 8.84 (d, 1.0) $N_4$, 8.42 (s) $A_2$, 8.21 (t, 0.7) $N_5$, 8.11 (s) $A_8$, 6.10 (d, 5.2 Hz) $N_{1'}$, 6.02 (d,) $A_{1'}$, 4.77 (t,) $A_{2'}$, 4.77 (t,) $A_{2'}$, 4.56 (br s), 4.51(br s), 4.45 (br s), 4.40 (br s), 4.26(br s).

NADPH
$^1H$ ($D_2O$): δ 8.48 (s) $A_8$, 8.21 (s) $A_2$, 6.94 (s) $N_6$, 6.13 (d,) $A_{1'}$, 5.98 (d, 0.7) $N_{1'}$, 8.11 (s) $A_8$, 6.10 (d, 5.2 Hz) $N_{1'}$, 6.02 (d,) $A_{1'}$, 4.78 (t,) $A_{2'}$, 4.71 (t,) $A_{2'}$, 4.51 (t,), 4.39 (br s), 4.22 (br m), 4.09 (br s), 2.71 (dd,) $P_4$

EXAMPLE 4

Example 4 demonstrates that the ruthenium catalyst $[Cl_2Ru(TPPTS)_2]_2$ is a catalyst precursor for the reduction of $NAD^+$ with $H_2$.

$NAD^+$ (34.0 mg, 38.0 µmol) was placed in 2 mL of a 0.1 M phosphate buffer. The pH of this solution was adjusted to 8.1 with NaOH and then placed in an 80 mL Fisher-Porter bottle. The Fisher-Porter bottle was evacuated and refilled with argon three times then $[Cl_2Ru(TPPTS)_2]_2$ (6.9 mg, 2.6 µmol) was added under a flow of argon. The Fisher-Porter bottle was evacuated and filled with 70 psi of $H_2$ and stirred to 23° C. for 17.0 hr. The volatiles were removed under reduced pressure and a sample dissolved in $D_2O$ To this was added 20 µl of trimethylsilylpropionate standard solution. $^1H$ NMR integration shows that 9.2 µmole of NADH have been produced under these conditions.

$NAD^+$
$^1H(D_2O)$: δ 9.35 (s) $N_2$, 9.17 (d, 0.6 Hz) $N_6$, 8.84 (d, 1.0) $N_4$, 8.42 (s) $A_2$, 8.21 (t. 0.7) $N_5$, 8.11(s) $A_8$, 6.10 (d, 5.2 Hz) $N_{1'}$, 6.02 (d,) $A_{1'}$, 4.77 (t,) $A_{2'}$, 4.56 (br s), 4.51 (br s), 4.45 (br s), 4.40 (br s), 4.26 (br s).

NADH
$^1H(D_2O)$: δ 8.48 (s) $A_8$, 8.21 (s) $A_2$, 6.94 (s) $N_6$, 6.13 (d,) $A_{1'}$, 5.98 (d, 0.7) $N_{1'}$, 8.11 (s) $A_8$, 6.10 (d, 5.2 Hz) $N_{1'}$, 6.02 (d,) $A_{1'}$, 4.78 (t,) $A_2$, 4.71 (t,) $A_{2'}$, 4.51 (t,), 4.39 (br s), 4.22 (br m), 4.09 (br s), 2.71 (dd,) $P_4$.

EXAMPLE 5

Example 5 demonstrates that iodide is not a poison for the catalyst derived from ruthenium complex $[Cl_2Ru(TPPTS)_2]_2$.

$NAD^+$ (34.0 mg, 38.0 µmol) was placed in 2 mL of a 0.1 M phosphate buffer containing 0.07 M sodium iodide. The pH of this solution was adjusted to 8.1 with NaOH and then placed in an 80 mL Fisher-Porter bottle. The Fisber-Porter bottle was evacuated and refilled with argon three times then [Cl$_2$Ru(TPPTS)$_2$]$_2$ (7.7 mg, 2.9 µmol) was added under a flow of argon. The Fisher-Porter bottle was evacuated and filled with 70 psi of H$_2$ and stirred to 23° C. for 13.0 hr. The volatiles were removed under reduced pressure and a sample dissolved in D$_2$O. To this was added 20 µl of trimethylsilylpropionate standard solution. $^1$H NMR integration shows that 7.4 µmole of NADH have been produced under these conditions.

EXAMPLE 6

Example 6 demonstrates that other water-soluble ruthenium complexes are catalysts for cofactor regeneration with H$_2$.

Using a procedure identical to that of Example 4 above Cl$_2$Ru(PTA)$_4$ (4.8 mg, 6.0 µmol) and NAD$^+$ (33.0 mg, 50.0 µmol) were reacted at 70 psi and 40° C. for 15.5 hr. $^1$H NMR assay shows that 11.0 µmole of NADH have been produced under these conditions.

EXAMPLE 7

Example 7 demonstrates that the phosphine ligands used in the above examples in ruthenium complexes are necessary to generate catalysts for cofactor regeneration.

Using a procedure identical to that of Example 4 above RuCl$_3$-hydrate (1.6 mg, 38.4% Ru, 6.0 µmol) and NAD$^+$ (33.0 mg, 50.0 µmol) were reacted at 70 psi and 40° C. for 2.5 hr. $^1$H NMR assay shows that no NADH has been produced under these conditions.

EXAMPLE 8

Example 8 demonstrates that the ruthenium complexes used in the above examples are necessary for the regeneration of cofactor with hydrogen.

Following the procedure of Example 4, but excluding the ruthenium catalyst, NAD$^+$ (33.0 mg, 50.0 µmol) was placed 2 mL of a 0.1 M (aq) KHPO$_4$ with 0.07 M sodium iodide in an 80 mL Fisher-Porter bottle and the pH adjusted to 8.15 with NaOH. After establishing a H$_2$-atmosphere (70 psig) and heating to 40° C. for 2.5 hr $^1$H NMR analysis showed no production of NADH.

EXAMPLE 9

Example 9 demonstrates that the hydrogen is necessary for the regeneration of cofactors described in the above examples.

Following the procedure of Example 4, [Cl$_2$Ru (TPPTS)$_2$]$_2$ (7.9 mg, 6.0 µmol) and NAD$^+$ (33.0 mg, 50.0 µmol) was placed 2 mL of 0.1 M (aq) KHPO$_4$ with 0.07 M sodium iodide and an atmosphere of argon rather than H$_2$, was placed over the reaction solution. After heating to 40° C. for 2.5 hr. $^1$H NMR analysis showed no NADH. The argon atmosphere was then replaced by H$_2$ and NADH was produced without significant catalyst deactivation.

EXAMPLE 10

Example 10 demonstrates that the TPPTS can be used as a stabilizer for TBADH.

Phosphate buffer (10 mL, 0.1 M, pH=7.0) was placed in a 100 mL Schlenk tube under argon. 2-Heptanone (4.92 g, 43.1 mmol), isopropanol (1.57 g, 26.1 mmol), heptadecane (41.0 µl), TPPTS (23 mg, 40.0 µmol), NADP$^+$ (0.4 mg, 0.5 µmol) and TBADH (2.7 mg, 19.8 units) were then added under a flow of argon. After evacuation and refilling with argon three times the apparatus was heated to 38° C. with an oil bath. GC analysis every five hours showed a continuous production of 2-heptanol for the initial 20 hours at a rate corresponding to~210 turnovers of NADP$^+$ per hour (total of 2.17 mmoles of 2-heptanol in 21 hours). After and additional 24 hours the yield of 2-heptanol had not changed. The final yield of 2-heptanol corresponds to 4,343 turnovers of NADP$^+$.

Comparative Example 10a

Comparative Example 10a shows TBADH productivity without a stabilizer.

Identical amounts of all reagents in a 2-heptanone reduction with isopropanol (Example 10) except for the water-soluble phosphine (TPPTS) were heated to 38° C. with an oil bath for 23 hours. The yield of 2-heptanol was 0.13 mmol, corresponding to a total of 271 turnovers of NADP$^+$.

Comparative Example 10b

Comparative Example 10b shows TBADH productivity with dithiothreitol (DTT) as a stabilizer.

Using the procedure described in Comparative Example 10a, identical amounts of all reagents except twice the amount of 2-heptanone (9.84, 86.2 mmol) and substituting DTT as a stabilizer (6 mg, 40 µmol) in place of TPPTS, the reduction of 2-heptanone with isopropanol was carried out at 38° C. for 19 hours yielding 2.51 mmol of 2-heptanol, corresponding to a total of 5,021 turnovers of NADP$^+$.

Comparative Example 10c

Comparative Example 10c shows TBADH productivity with mercaptoethanol as a stabilizer.

Using the procedure described in Example 10 and identical amounts of all reagents but substituting mercaptoethanol as a stabilizer (2.8 µl, 40 µmol) in place of DTT, the reduction of 2-heptanone with isopropanol was carried out at 38° C. for 22 hours yielding 2.56 mmol of 2-heptanol, corresponding to a total of 5,121 turnovers of NADP$^+$.

EXAMPLE 11

Example 11 demonstrates that triphenylphosphine (TPP) can be used as a stabilizer for TBADH.

Using the procedure described in Example 10 and identical amounts of all reagents but substituting triphenylphosphine as a stabilizer (10 mg, 40 µmol) in place of TPPTS, the reduction of 2-heptanone with isopropanol was carried out at 37° C. for 19 hours yielding 2.15 mmol of 2-heptanol, corresponding to a total of 4,301 turnovers of NADP$^+$.

EXAMPLE 12

Example 12 demonstrates that "monosulfonated triphenylphosphine" (TPPMS) can be used as a stabilizer for TBADH.

Using the procedure describe in Example 10 and identical amounts of all reagents but substituting triphenylphosphine as a stabilizer (15 mg, 40 µmol) in place of TPPTS, the reduction of 2-heptanone with isopropanol was carried out at 38° C. for 16 hours yielding 1.93 mmol of 2-heptanol, corresponding to a total of 3,859 turnovers of NADP$^+$.

Throughout this application, various publications are referenced. The disclosures of these publications in their entireties are hereby incorporated by reference into this application.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A process for stabilizing the activity of an oxidoreductase enzyme, comprising mixing a phosphine or phosphite with an oxidoreductase enzyme.

2. The process of claim 1, wherein the phosphine or the phosphite comprise phosphorus derivatives $PR_n(O-R)_{3-n}$, wherein ii is an integer from zero to three, the R groups may be the same or different and the R groups comprise hydrocarbyl, substituted hydrocarbyl, aromatic or heteroaromatic groups.

3. The process of claim 2, wherein the one or mare R groups are substituted with one or more polar groups.

4. The process of claim 3, wherein the polar group comprises sulfonate, carboxylate, amino, alkylammonium, hydroxyl, or polyalkylene glycol groups.

5. The process of claim 1, wherein the mixing occurs in a liquid medium.

6. The process of claim 1, wherein the oxidoreductase enzyme is an enzyme characterized under the EC classification system as having a first digit EC classification off 1.

7. The process of claim 1, wherein the oxidoreductase enzyme is a nicotinamide cofactor dependent enzyme.

8. The process of claim 1, wherein the oxididoreductase enzyme comprises a cysteine amino acid residue.

9. The process of claim 1, wherein the rate of loss of activity of oxidoreductase enzyme is slower in the presence of the phosphite or phosphite as compared to the rate of loss of activity of the oxidoreductase enzyme in the absence of the phosphine or phosphite.

10. The process of claim 5, wherein the liquid medium comprises water, an organic solvent, or a mixture thereof.

11. The process of claim 5, wherein the liquid medium is a substantially aqueous buffer solution.

12. The process of claim 1, wherein the phosphine or phosphite compound has one or more anionic sulfonate groups.

13. The process of claim 1, wherein the phosphine compound is a salt of tris(m-sulfonatophenyl)phosphine.

14. The process of claim 1, wherein the phosphine or phosphite is a water soluble phosphine or phosphite.

* * * * *

UNITED STATES PATENT AND TRADEMARK OFFICE
CERTIFICATE OF CORRECTION

PATENT NO.      : 7,195,889 B2                                        Page 1 of 1
APPLICATION NO. : 10/308778
DATED           : March 27, 2007
INVENTOR(S)     : Robert T. Hembre et al.

It is certified that error appears in the above-identified patent and that said Letters Patent is hereby corrected as shown below:

On Title Page 1, under the section entitled "Related U.S. Application Data (60)," delete "60/123,888" and substitute the following:
   --60/123,833--

Column 25
Line 20, delete "ii" and substitute the following --n--.

Column 26
Line 5, delete "off" and substitute the following --of--.

Lines 10-11, delete "rate of loss of activity of oxidoreductase enzyme is slower" and
       substitute the following --oxidoreductase enzyme loses activity more slowly--

Lines 12-13, delete "as compared to the rate of loss of activity of the oxidoreductase enzyme" and substitute the following:
   --than--

Signed and Sealed this

Eighteenth Day of December, 2007

JON W. DUDAS
*Director of the United States Patent and Trademark Office*